United States Patent
Yoshimoto et al.

(10) Patent No.: US 12,285,599 B2
(45) Date of Patent: Apr. 29, 2025

(54) TUBE PUMP

(71) Applicant: SHIBUYA CORPORATION, Kanazawa (JP)

(72) Inventors: Kenshi Yoshimoto, Kanazawa (JP); Kosho Matsuzaki, Kanazawa (JP)

(73) Assignee: SHIBUYA CORPORATION, Kanazawa (JP)

( * ) Notice: Subject to any disclaimer, the term of this patent is extended or adjusted under 35 U.S.C. 154(b) by 79 days.

(21) Appl. No.: 18/325,310

(22) Filed: May 30, 2023

(65) Prior Publication Data

US 2023/0405202 A1 Dec. 21, 2023

(30) Foreign Application Priority Data

Jun. 17, 2022 (JP) .................. 2022-098158

(51) Int. Cl.
*A61M 60/835* (2021.01)
*A61M 60/279* (2021.01)
*F04B 43/12* (2006.01)

(52) U.S. Cl.
CPC ....... *A61M 60/835* (2021.01); *F04B 43/1253* (2013.01); *A61M 60/279* (2021.01)

(58) Field of Classification Search
CPC ............ A61M 1/36225; A61M 60/835; A61M 60/279; F04B 43/1253; F04B 43/12
See application file for complete search history.

(56) References Cited

U.S. PATENT DOCUMENTS

| | | | |
|---|---|---|---|
| 2002/0064470 A1* | 5/2002 | Andersen ............ | A61M 60/279 417/477.3 |
| 2007/0296744 A1* | 12/2007 | Kubota ............... | F04B 43/1253 347/7 |
| 2021/0277884 A1* | 9/2021 | Buckle .................... | F04B 53/00 |

FOREIGN PATENT DOCUMENTS

| | | |
|---|---|---|
| JP | 617769 A | 1/1994 |
| JP | 5397747 B2 | 9/2010 |

* cited by examiner

*Primary Examiner* — David N Brandt
(74) *Attorney, Agent, or Firm* — FLYNN THIEL, P.C.

(57) ABSTRACT

A tube pump having a housing in which a large diameter flexible tube is arranged along a lateral wall formed to have a substantially horseshoe shape, and a roller that moves along the lateral wall of the housing. Between a blockage section which pressures and blocks the large diameter tube and a separation section shaped so as to gradually extend away from the rotation center, the lateral wall is provided with a pressure release section having an arc with a radius larger than the blockage section. While the roller is moving through the pressure release section, a communication opening is formed in the large diameter tube pressured by the roller so as to allow communication between a part positioned on an upstream side and a part positioned on a downstream side of the roller, while a size of the communication opening is maintained to constant.

3 Claims, 2 Drawing Sheets

TUBE PUMP

BACKGROUND OF THE INVENTION

Field of the Invention

The present invention is related to a tube pump and, more specifically, related to a tube pump that pumps fluid by pressing and moving a flexible tube with a roller.

Description of the Related Art

Conventionally, a dialysis apparatus for dialysis treatment, for example, uses a tube pump as a blood pump that pumps blood of a patient. Such a tube pump includes: a housing in which a flexible tube is arranged along a lateral wall formed to have a substantially horseshoe shape; a rotor rotatably provided inside the lateral wall of the housing; and a roller provided for the rotor so as to move along the lateral wall.

When the rotor is rotated, as a result of the roller moving while pressing the flexible tube, fluid in the flexible tube is pumped (Japanese Patent No. 5397747).

The lateral wall of the housing of such a tube pump has formed therewith: a blockage section in which the flexible tube is pressed and completely blocked between the roller and the lateral wall; and a separation section that is contiguously provided on the downstream side of the blockage section and is shaped so as to gradually distance away from the rotation center of the rotor.

In the separation section, because the pressure from the roller on the tube is resolved, the flexible tube has a tendency to return to an original shape with elasticity thereof. The volume of the part that has so far been pressed by the roller thus increases.

In that situation, if the roller drastically becomes separate from the lateral wall, because the volume of the part that has so far been pressed increases drastically, the fluid in the vicinity is drawn in. In particular, when the fluid positioned on the downstream side of the rotor is drawn in, a problem arises where pulsation is caused in the circuit by backflow of the fluid.

To cope with this problem, in a tube pump disclosed in Japanese Laid-Open Patent Application No. 6-17769, the roller is configured to gradually distance away from the lateral wall in the separation section described above, so as to inhibit backflow of the fluid by ensuring that the volume of the part that has so far been pressed by the rotor does not increase quickly.

However, even in such a tube pump, when a tool that may cause resistance to the flow of the fluid such as a dialyzer, for example, is provided on the downstream side of the tube pump, pumping pressure from the tube pump and pressure from the resistance caused by the tool act on the fluid flowing between the tube pump and the tool.

As a result, the pressure of the fluid positioned on the downstream side of the roller moving through the blockage section becomes higher than the pressure of the fluid positioned on the upstream side of the roller, and a pressure difference thus occurs between the two.

Consequently, when the rotor has distanced away from the lateral wall in the separation section, so that a communication opening is formed in the flexible tube so as to allow communication between the parts positioned on the upstream side and the downstream side of the rotor, a problem arises where the fluid passing through the communication opening backflows so as to solve the pressure difference, which may cause pulsation.

In view of the problem described above, the present invention is to provide a tube pump capable of more effectively inhibiting pulsation of the fluid in a flexible tube.

SUMMARY OF THE INVENTION

More specifically, a tube pump according to one aspect of the invention includes: a housing in which a flexible tube is arranged along a lateral wall formed to have a substantially horseshoe shape; a rotor rotatably provided inside the lateral wall of the housing; and a roller provided for the rotor so as to move along the lateral wall, wherein the lateral wall is provided with a blockage section which has an arc with a prescribed radius centered on a rotation center of the rotor and which presses and blocks the flexible tube between the roller and the lateral wall and a separation section which is provided on a downstream side of the blockage section and which is shaped so as to gradually distance away from the rotation center, the tube pump being characterized in that the lateral wall is provided, between the blockage section and the separation section, with a pressure release section which has an arc centered on the rotation center of the rotor while having a radius larger than that of the blockage section, and while the roller is moving through the pressure release section, a communication opening is formed in the flexible tube pressured by the roller so as to allow communication between a part positioned on an upstream side and a part positioned on a downstream side of the roller, while a size of the communication opening is maintained to be constant.

According to the aspect of the invention described above, by providing the pressure release section between the blockage section and the separation section, the small communication opening is formed in the pressured flexible tube between the parts positioned on the upstream side and the downstream side of the roller. In addition, while the roller passes through the pressure release section, the size of the communication opening is kept constant.

With these arrangements, it is possible to solve the pressure difference between the space positioned on the upstream side and the space positioned on the downstream side of the roller, by forming a small flow that travels from the downstream side toward the upstream side of the roller via the communication opening. Consequently, even when the roller subsequently moves to the separation section and becomes separate from the flexible tube, the backflow of the fluid that may be caused by the pressure difference is inhibited. It is therefore possible to inhibit the occurrence of the pulsation.

DETAILED DESCRIPTION

Figure 1:
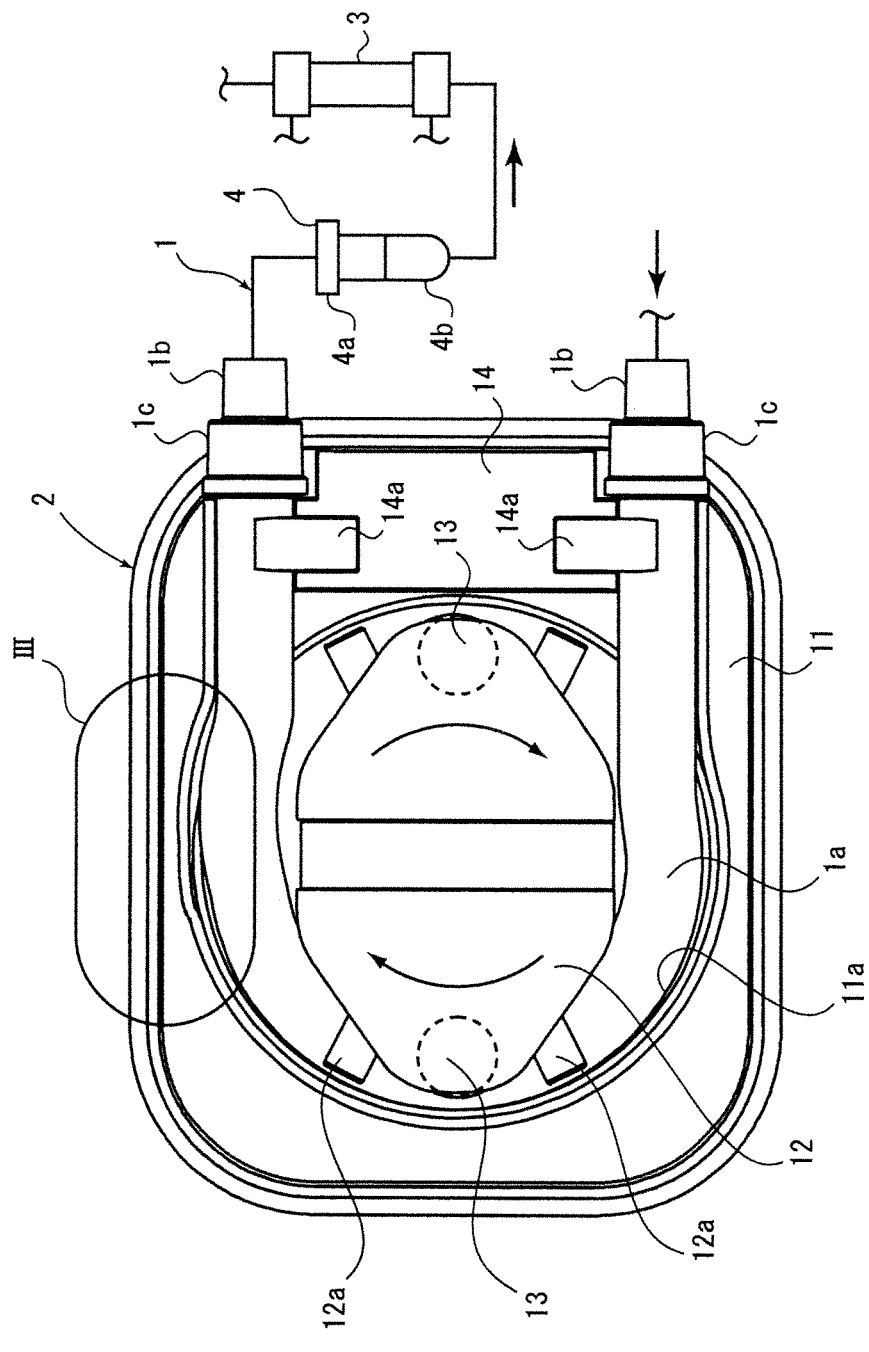
FIG. 1 is a plan view of a tube pump.

The following will describe an embodiment shown in the drawings. FIG. 1 shows a tube pump 2 provided for a blood circuit 1 structuring a dialysis apparatus. The blood circuit 1 is provided with a dialyzer 3 for performing blood dialysis and a drip chamber 4.

The blood circuit 1 is configured so as to include an artery side blood circuit and a vein side blood circuit, by using a flexible tube having elasticity. An end part of the artery side blood circuit and an end part of the vein side blood circuit are each to be connected to a blood vessel of a patient. Further, the blood that has entered from the artery side is dialyzed with a dialysis fluid in the dialyzer 3, before being discharged on the vein side.

Further, in the present embodiment, the tube pump 2 is provided on the upstream side (i.e., the artery side) of the dialyzer 3. In addition, the drip chamber 4 is provided between the tube pump 2 and the dialyzer 3.

The drip chamber 4 is provided, at the center thereof, with a cap 4a to which the flexible tube on the tube pump 2 side is attached and is provided, in a lower end part thereof, a case 4b to which the flexible tube on the dialyzer 3 side is attached. The cap 4a and the case 4b are hermetically closed while being kept airtight.

As for the flexible tube attached to the cap 4a, a tip end part thereof is positioned inside the case 4b. The blood pumped by the tube pump 2 drips into the case 4b from the tip end of the flexible tube connected above the drip chamber 4 and is subsequently pumped to the dialyzer 3 through the flexible tube connected underneath the case 4b.

The tube pump 2 includes: a housing 11 in which the flexible tube is arranged along a lateral wall 11a formed to have a substantially horseshoe shape; a rotor 12 rotatably provided inside the lateral wall 11a of the housing 11; and rollers 13 provided for the rotor 12 so as to move along the lateral wall 11a. The rotor 12 is to be driven by a motor (not shown).

Of the flexible tube structuring the blood circuit 1, in the part attached to the tube pump 2, a large diameter tube 1a having a larger diameter than in the other part is used. To each of the two end parts of the large diameter tube 1a, a small diameter tube 1b is connected via a connector 1c.

In the present embodiment, the small diameter tube 1b, connected to the end part of the large diameter tube 1a and illustrated on the lower side in the drawing, is to be attached to the artery side of the patient. The small diameter tube 1b connected to the end part illustrated on the upper side in the drawing is to be connected to the vein side of the patient, i.e., to the dialyzer 3.

In the present embodiment, used as the large diameter tube 1a is a tube having an outside diameter of 12 mm and an inside diameter of 8 mm. Used as the small diameter tube 1b is a tube having an outside diameter of 6.6 mm and an inside diameter of 4.4 mm.

Figure 2:
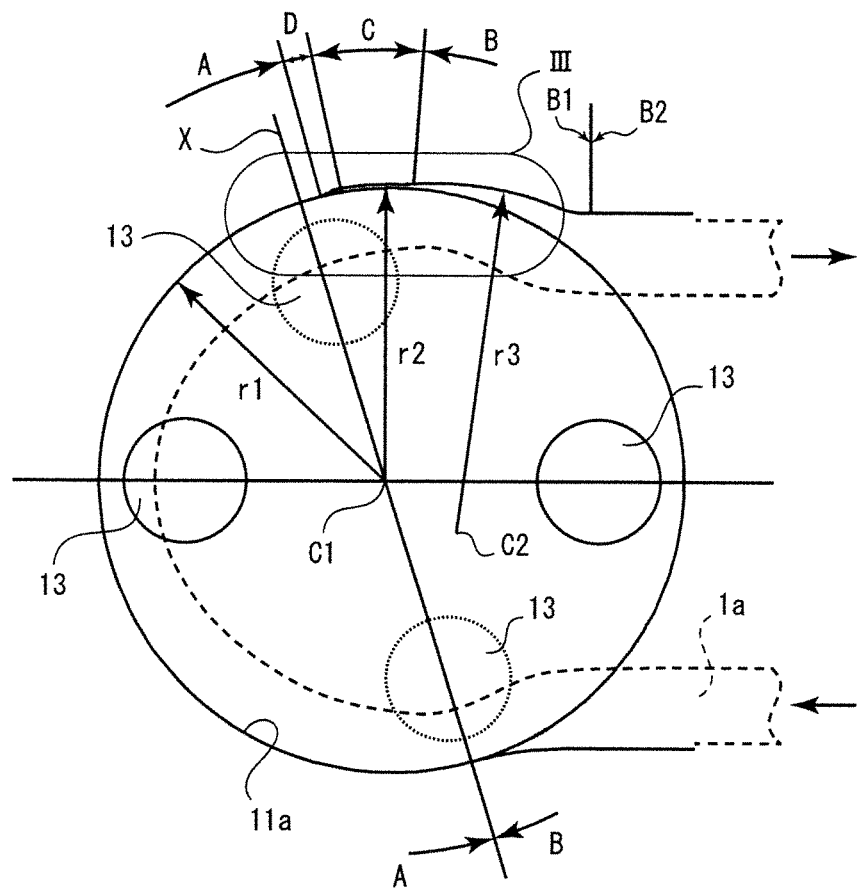
FIG. 2 is a drawing for explaining movement of the rollers.

As shown in FIG. 2, the lateral wall 11a formed in the housing 11 so as to have the substantially horseshoe shape has: a blockage section A which has an arc with a radius r1 centered on a rotation center C1 of the rotor 12; and separation sections B provided adjacent to the blockage section A on the upstream side and on the downstream side thereof, in the rotation direction of the rotor 12.

Although the shape of the separation sections B will be explained in detail later, parts thereof include support sections B2 in each of which the lateral walls 11a structuring, or forming the structure of, the separation section B oppose each other in parallel. When the large diameter tube 1a is to be attached to the housing 11, the end parts of the large diameter tube 1a positioned on the upstream side and the downstream side are placed in the support sections B2.

Further, as shown in FIG. 1, provided between the two lateral walls 11a structuring the support sections B2 are a holding block 14 for holding the large diameter tube 1a in the housing 11 and grip pieces 14a provided for the holding block 14.

In addition, in the housing 11, at end parts of the separation sections B and end parts of the holding block 14, engagement parts are formed so as to be each engaged with a different one of the connectors 1c provided at the two ends of the large diameter tube 1a.

With this configuration, when the large diameter tube 1a is to be attached to the tube pump 2, to begin with, while the connectors 1c are engaged with the engagement parts, the large diameter tube 1a is arranged along the lateral wall 11a, so as to subsequently have the end parts of the large diameter tube 1a held by the grip pieces 14a by fixing the holding block 14 onto the housing 11.

In the present embodiment, the rotor 12 rotates clockwise as shown in the drawing. The two rollers 13 are positioned so as to oppose each other while the rotation center C1 of the rotor 12 is interposed therebetween. Each of the rollers 13 is maintained by a spring (not shown) in a biased state toward the outside of the rotor 12.

Further, the rotor 12 is provided with guide pins 12a in positions adjacent to each of the rollers 13 on the upstream side and on the downstream side in the rotation direction, so as to prevent the large diameter tube 1a from falling off while the rotor 12 is rotating.

In the present embodiment, the diameter of each of the rollers 13 is 18 mm. Also, because of the outward bias caused by the spring, the center of each of the rollers 13 moves at a position with a radius of 30.3 mm from the rotation center C1 of the rotor 12.

In contrast, when the large diameter tube 1a is pressed by either of the rollers 13, because the roller 13 moves toward the rotation center C1 against the force of the spring, the center of the roller 13 moves at a position with a radius of 30 mm from the rotation center C1 of the rotor 12. In other words, the rollers 13 are able to move in the radial direction by 0.3 mm.

Next, the blockage section A set with the lateral wall 11a of the housing 11 has an arc shape with the radius r1 centered on the rotation center C1 of the rotor 12. In the present embodiment, the radius r1 is set to be 42.5 mm.

While either of the rollers 13 is moving through the blockage section A, the roller 13 presses the large diameter tube 1a against the lateral wall 11a, so as to block communication between the space positioned on the upstream side and the space positioned on the downstream side of the position of the roller 13.

As a result, while either of the rollers 13 is moving through the blockage section A, because the part pressed by the roller 13 also moves, the fluid positioned on the downstream side of the pressed part is pumped toward the dialyzer 3 positioned on the downstream side.

Further, in the present embodiment, as shown in FIG. 2, the blockage section A is formed in the range of at least 180°. Accordingly, when the two rollers 13 are positioned in the blockage section A at the same time (the state X in the drawing), the large diameter tube 1a between the two rollers 13 is hermetically sealed by the two rollers 13.

Figure 3:
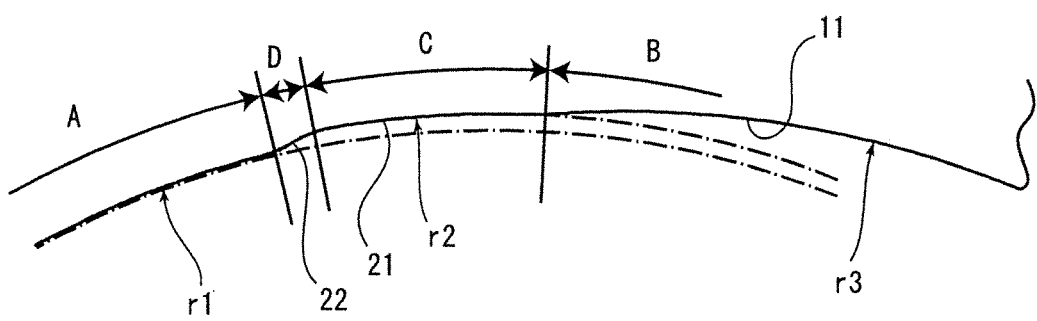
FIG. 3 is an enlarged view of section III in FIG. 1 and FIG. 2.

FIG. 3 is an enlarged view of section III in FIG. 1 and FIG. 2. The separation section B is provided on the downstream side, in the rotation direction of the rotor 12, of the blockage section A. The tube pump 2 in the present embodiment is characterized in that a pressure release section C is provided between the blockage section A and the separation section B.

At first, the pressure release section C will be explained. The pressure release section C is structured with an arc plane 21 with a radius of r2. Formed between the blockage section A and the pressure release section C is a connection section D having a sloped plane 22.

The arc plane 21 has the radius r2 that is larger than the radius of the lateral wall 11a structuring the blockage section A. In the present embodiment, the radius r2 of the arc plane 21 is set to be 43.1 mm.

In this situation, when the radius r1 of the blockage section A is expressed as 100, it is desirable to configure the percentage of the radius r2 of the arc plane 21 to be in the range of 101.4% to 101.7%, while taking into consideration the size of an opening part formed in the large diameter tube 1a, which is explained later.

The sloped plane 22 is formed between the blockage section A and the arc plane 21. A boundary part between the blockage section A and the sloped plane 22, as well as another boundary part between the sloped plane 22 and the arc plane 21 are each smoothly connected.

With this configuration, when either of the rollers 13 moves to the arc plane 21 of the pressure release section C, the pressure of the roller 13 imposed on the large diameter tube 1a weakens.

As a result, the large diameter tube 1a has a tendency to return to the original shape with elasticity thereof. Accordingly, a communication opening is formed in the part that has so far been blocked by the roller 13, so as to allow communication between the space positioned on the upstream side and the space positioned on the downstream side of the roller 13.

It is desirable to form the communication opening so as to have a size in the range of 0.1 mm to 0.2 mm or in the range of 1.3% to 2.5% of the inside diameter of the large diameter tube 1a.

When the size of the communication opening is smaller than 1.3% of the inside diameter of the large diameter tube 1a, there is a possibility that advantageous effects explained below might not sufficiently be exerted, because the fluid would hardly flow between the space positioned on the upstream side and the space positioned on the downstream side of the roller 13.

On the contrary, when the size of the communication opening exceeds 2.5% of the inside diameter of the large diameter tube 1a, the communication opening would be too large, and it would not be possible to inhibit the pulsation because the fluid would be allowed to flow in a large volume between the space positioned on the upstream side and the space positioned on the downstream side of the roller 13.

Further, it is also possible to adjust the size of the communication opening formed in the large diameter tube 1a, depending on the difference between the radius r1 of the blockage section A and the radius r2 of the arc plane 21 of the pressure release section C, the bias force of the spring biasing the rollers 13, and the movement amounts of the rollers 13 in the radial direction.

The separation sections B include: flattening amount variable sections B1 in which the lateral wall 11a is formed so as to gradually distance away from the rotation center C1 of the rotor 12; and the support sections B2 formed horizontally as shown in the drawing so as to support the end parts of the large diameter tube 1a where the rotor 12 is separate from the flexible tube.

The shape of the lateral wall 11a in the flattening amount variable section B1 is set so that the pressure on the large diameter tube 1a gradually decreases as the rollers 13 move. More specifically, the setting is such that a volume Vin of the fluid pumped by either of the rollers 13 is no smaller than a volume Vout indicating an increase caused by the restoration of the large diameter tube 1a when the roller 13 becomes separate from the large diameter tube 1a (the volume Vin−the volume Vout >0).

First of all, the volume Vout denotes the increase amount in the volume inside the large diameter tube 1a, caused by the restoration of the large diameter tube 1a with the elasticity thereof when the pressure applied to the large diameter tube 1a by either of the rollers 13 is resolved while the roller 13 is moving through the flattening amount variable section B1.

In contrast, the volume Vin denotes a pumped amount of the fluid positioned on the downstream side of the part pressed by either of the rollers 13, when the roller 13 moves through the blockage section A by the same distance as the distance by which the roller 13 moves through the flattening amount variable section B1.

As explained herein, the lateral wall 11a in the flattening amount variable section B1 is set to be distant from the roller 13 in order to satisfy the relation expression "The volume Vin−the volume Vout >0". In the present embodiment, as shown in FIG. 2, the flattening amount variable section B1 has an arc shape with a radius r3 centered on a center C2, which deviates from the rotation center C1 of the rotor 12.

Next, an operation of the tube pump 2 having the configuration described above will be explained. To begin with, the tube pump 2 is attached to the blood circuit 1 of the dialysis apparatus, and the large diameter tube 1a is installed in the housing 11, as shown in FIG. 1.

After that, when priming preparation for the blood circuit 1 is completed, and dialysis treatment using the dialysis apparatus is started, the rotor 12 of the tube pump 2 rotates, so that the tube pump 2 draws blood from a blood vessel (an artery) of the patient and pumps the blood toward the dialyzer 3.

Further, in the dialyzer 3, while the blood is passing through a blood chamber formed in the dialyzer 3, dialysis is carried out with the dialysis fluid flowing through a dialysis fluid chamber. After that, the blood that has passed through the blood chamber is returned to a blood vessel (a vein) of the patient.

In the tube pump 2, as the rotor 12 rotates, while either of the rollers 13 is moving through the blockage section A, the part of the large diameter tube 1a pressed by the roller 13 moves, so that the blood positioned on the downstream side of the roller 13 is pumped so as to be pushed out toward the dialyzer 3.

In this situation, when the tube pump 2 pumps the blood toward the dialyzer 3, resistance occurs when the blood passes through the dialyzer 3. Because of the pressure of the pumping by the tube pump 2 and the resistance occurring during the passing through the dialyzer 3, the internal pressure in the flexible tube between the tube pump 2 and the dialyzer 3 becomes positive pressure.

In contrast, in the blockage section A, because the large diameter tube 1a is pressed by the roller 13, communication is blocked between the spaces positioned on the upstream side and the downstream side of the roller 13. Accordingly, a pressure difference occurs between the space positioned on the upstream side and the space positioned on the downstream side of the roller 13.

Subsequently, when the roller 13 has moved from the blockage section A to the pressure release section C, because the lateral wall 11a is positioned distant with respect to the rotation center C1 of the rotor 12, the pressure applied to the large diameter tube 1a by the roller 13 decreases, so that the small communication opening is formed in the large diameter tube 1a so as to allow communication between the space positioned on the upstream side and the space positioned on the downstream side of the roller 13.

Because the pressure in the space positioned on the downstream side of the roller 13 is higher than the pressure in the space positioned on the upstream side, the blood that has so far been positioned on the downstream side of the roller 13 would have a tendency to backflow toward the space positioned on the upstream side.

In the present embodiment, the pressure release section C has, in the range described above, the arc shape positioned distant from the rotation center C1 of the rotor 12. Consequently, the communication opening is smaller than the original inside diameter of the large diameter tube 1a. In addition, the size of the communication opening is kept constant until the roller 13 passes through the pressure release section C.

With this configuration, until the roller 13 gets past the pressure release section C, it is possible to cause the blood to flow in a small volume from the space positioned on the upstream side to the space positioned on the downstream side of the roller 13. It is therefore possible to gradually resolve or decrease the pressure difference between the space positioned on the upstream side and the space positioned on the downstream side of the roller 13.

In other words, it is possible to inhibit the blood positioned on the downstream side of the roller 13 from drastically backflowing toward the space positioned on the upstream side. It is therefore possible to inhibit the pulsation of the blood on the downstream side of the tube pump 2.

Subsequently, when the roller 13 has moved from the pressure release section C to the flattening amount variable section B1 of the separation section B, the lateral wall 11a gradually distances away from the rotation center C1 of the rotor 12, so as to enlarge the communication opening allowing the commination between the space positioned on the upstream side and the space positioned on the downstream side of the roller 13.

When the communication opening enlarges in this manner, the large diameter tube 1a in the part that has so far been pressed by the roller 13 has a tendency to return to the original shape with the elasticity thereof, which allows the volume of the part that has so far been pressed by the roller 13 to gradually increase.

When the volume increases, the blood positioned in the vicinity of the part that has so far been pressed by the roller 13 is drawn into the volume-increased part. In particular, the blood that has so far been positioned on the downstream side of the roller 13 would have a tendency to backflow.

However, as explained above, the flattening amount variable section B1 of the present embodiment is set in such a manner that the pumped volume Vin of the fluid pumped by the roller 13 is no smaller than the volume Vout indicating the increase caused by the restoration of the flexible tube.

As a result, while the roller 13 is moving through the flattening amount variable section B1, although the volume Vout of the part of the large diameter tube 1a that had been pressed by the roller 13 gradually increases, the volume Vin of the pumped fluid is still larger. Accordingly, it is possible to inhibit the backflow of the blood positioned on the downstream side of the roller 13. It is therefore possible to inhibit the pulsation of the blood in the blood circuit 1.

Further, with the tube pump 2 provided with the pressure release section C according to the present embodiment, we evaluated advantageous effects of inhibiting the backflow of the blood. For this evaluation, as a comparison, another tube pump 2 was prepared in which the position of the pressure release section C was formed as a blockage section A, while the rest of the dimensions were the same.

To begin with, similarly to the example of performing dialysis treatment, the flexible tube structuring the blood circuit 1 was installed in the tube pump 2. To the flexible tube, the dialyzer 3 and the drip chamber 4 were connected.

After that, similarly to the dialysis treatment, the tube pump 2 was brought into operation, so that blood (water in the present example) was pumped from the tube pump 2 via the drip chamber 4 to the dialyzer 3, so as to observe a tip end part of the flexible tube placed inside the drip chamber 4.

As explained above, because the tip end of the flexible tube provided on the tube pump 2 side is placed inside the case 4b through the cap 4a of the drip chamber 4, when the fluid backflows in the tube pump 2, the fluid that was once pumped as far as to the tip end of the flexible tube retreats, so that air from the inside of the drip chamber 4 enters the tip end of the tube.

Thus, in the present evaluation, magnitudes of backflow were evaluated by measuring a maximum distance (a maximum retreat amount) from the tip end of the flexible tube to a tip end part of the fluid, when the fluid was pumped by the tube pump 2, and the fluid that reached the tip end of the flexible tube backflowed.

Results of the experiment showed that the maximum retreat amount with the tube pump 2 according to the present embodiment was, on average, 14 mm. In contrast, the maximum retreat amount with the conventional tube pump 2 without the pressure release section C was, on average, 43 mm.

Consequently, it was confirmed that the backflow of the blood was inhibited to a minimum level, by using the tube pump 2 provided with the pressure release section C as described in the present embodiment.

Further, inhibiting the backflow of the blood in this manner makes it possible to inhibit the pulsation of the blood associated with the backflow. It is therefore possible to solve problems where air bubbles may occur in the drip chamber 4 and where effects of anticoagulants may be lowered.

In the above embodiment, the configuration was explained in which the dialyzer 3 is provided on the downstream side of the tube pump 2. However, the tube pump 2 of the present invention is suitable in various situations that are not limited to the dialyzer 3 but in which any tool that causes resistance to a flow of fluid is provided on the downstream side of the tube pump 2.

What is claimed is:

1. A tube pump comprising:
   a housing which houses a flexible tube is arranged along a lateral wall formed to have a substantially horseshoe shape;
   a rotor rotatably provided inside the lateral wall of the housing; and
   a roller provided for the rotor so as to move along the lateral wall, wherein
   the lateral wall is provided with a blockage section having an arc with a prescribed radius centered on a rotation center of the rotor and the blockage section presses and blocks the flexible tube between the roller and the lateral wall, and a separation section provided on a downstream side of the blockage section, the separation section being shaped so as to gradually distance away from the rotation center;

the lateral wall is provided, between the blockage section and the separation section, with a pressure release section having an arc centered on the rotation center of the rotor having a constant radius larger than the prescribed radius of the blockage section; and while the roller is moving through the pressure release section, a communication opening is formed in the flexible tube pressed by the roller so as to allow communication between apart of the flexible tube positioned on an upstream side of the roller and a part of the flexible tube positioned on a downstream side of the roller, while a size of the communication opening is maintained to be constant.

2. The tube pump according to claim 1, wherein the constant radius of the pressure release section is constant along an entire extent of the arc of the pressure release section.

3. The tube pump according to claim 2, wherein the size of the communication opening of the flexible tube is maintained constant by the constant radius of the pressure release section for an entire time the roller moves along the pressure release section.

* * * * *